(12) United States Patent
Miller et al.

(10) Patent No.: US 7,245,367 B2
(45) Date of Patent: Jul. 17, 2007

(54) METHOD AND APPARATUS FOR DETECTING CONTAMINANTS ON A WINDOW SURFACE OF A VIEWING SYSTEM UTILIZING LIGHT

(75) Inventors: Mark S. Miller, Apple Valley, MN (US); David M. Socha, Sr., Champlin, MN (US); Kaare J. Anderson, Farmington, MN (US)

(73) Assignee: Rosemount Aerospace Inc., Burnsville, MN (US)

( * ) Notice: Subject to any disclaimer, the term of this patent is extended or adjusted under 35 U.S.C. 154(b) by 409 days.

(21) Appl. No.: 10/769,968

(22) Filed: Feb. 2, 2004

(65) Prior Publication Data

US 2005/0168732 A1 Aug. 4, 2005

(51) Int. Cl.
*G01N 21/00* (2006.01)
*G01N 21/55* (2006.01)

(52) U.S. Cl. .................... 356/239.8; 356/445
(58) Field of Classification Search ............ 356/239.8, 356/446, 445; 318/483, DIG. 2
See application file for complete search history.

(56) References Cited

U.S. PATENT DOCUMENTS 6,603,137 B2 * 8/2003 Hochstein ............... 250/573

* cited by examiner

*Primary Examiner*—Hwa (Andrew) Lee
*Assistant Examiner*—Marissa J. Detschel
(74) *Attorney, Agent, or Firm*—Calfee, Halter & Griswold LLP

(57) ABSTRACT

A method of detecting contaminants on a window surface of a viewing system comprises the steps of: reflecting light off of contaminants on the window surface; capturing the reflected light in an image; converting the image into image data; and processing the image data to detect the contaminants on the window surface. Also, apparatus for detecting contaminants on an external surface of a window of a viewing system comprises: at least one light source for reflecting light from contaminants on the external surface; an imager for capturing an image of the reflected light and converting the image into image data; and a processor for processing the image data to detect the contaminants on the external surface. The apparatus may be embodied in a viewing system wherein the imager also captures images of a scene of the viewing system both including the light reflected from the contaminants and not including light reflected from contaminants; and the processor processes both of image data of the scene excluding reflected light from the contaminants, and image data of the scene including reflected light from the contaminants to detect the contaminants on the external surface.

25 Claims, 4 Drawing Sheets

METHOD AND APPARATUS FOR DETECTING CONTAMINANTS ON A WINDOW SURFACE OF A VIEWING SYSTEM UTILIZING LIGHT

BACKGROUND OF THE INVENTION

The present invention is related to detecting window contamination, in general, and more particular to a method and apparatus for detecting contaminants on a window surface of a viewing system utilizing light.

A windowed area is generally used to protect a viewer or viewing system from the environment of a viewing scene. Contaminants which may be particulates, such as dust, ice, water and the like, for example, may form on the outside window surface and obscure the view of the scene. A viewer can detect such contaminants and move his or her head to view the scene from a different perspective, thus avoiding the contaminants. However, in viewing systems, a camera may be located at a stationary position behind the window to view a scene through the window from a fixed perspective. Under these circumstances, any contaminants formed on the window in the viewing area of the camera will degrade the image produced by the camera.

Viewing systems which utilize automated image processing for a particular application are particularly vulnerable to contaminants forming on the viewing area of the window surface. Such systems may view the scene through a video or infrared camera, for example, which produce electrical signals representative of image frames of the scene. Each frame may be comprised of rows and columns of picture elements or pixels. Each electrical signal may be representative of the light intensity of each picture element of the frame. A signal processor may be used to process the pixel signals of each image frame to detect a change in a parameter viewed in the scene according to some predetermined criteria. If the camera images are not displayed to a person, contaminants formed in the viewing area of the window will go undetected. Such contaminants may affect the pixel signals and cause a false detection of a parameter change. Accordingly, decisions made by the image processing of the pixel signals will be compromised by the contaminants.

The present invention provides for a method and apparatus for detecting contaminants in the viewing area of the window surface utilizing light so that an operator may be made aware of such contaminants and a potential compromise of the decisions made by image processing of the pixel signals.

SUMMARY OF THE INVENTION

In accordance with one aspect of the present invention, a method of detecting contaminants on a window surface of a viewing system comprises the steps of: reflecting light off of contaminants on the window surface; capturing the reflected light in an image; converting the image into image data; and processing the image data to detect the contaminants on the window surface.

In accordance with another aspect of the present invention, apparatus for detecting contaminants on an external surface of a window of a viewing system comprises: at least one light source for reflecting light from contaminants on the external surface; an imager for capturing an image of the reflected light and converting the image into image data; and a processor for processing the image data to detect the contaminants on the external surface.

In accordance with yet another aspect of the present invention, a viewing system comprises: a window for protecting the viewing system from an environment of a scene viewable by the system; an imager disposed behind the window for capturing images of the scene through a viewing area of the window and for converting the images into image data; at least one light source disposed to inject light edgewise into the window to cause reflections of the injected light off of contaminants on the window surface, the imager also for capturing images of the scene including the light reflected from the contaminants; and a processor for processing both of image data of the scene excluding reflected light from the contaminants, and image data of the scene including reflected light from the contaminants to detect the contaminants on the external surface.

DETAILED DESCRIPTION OF THE INVENTION

Figure 1:
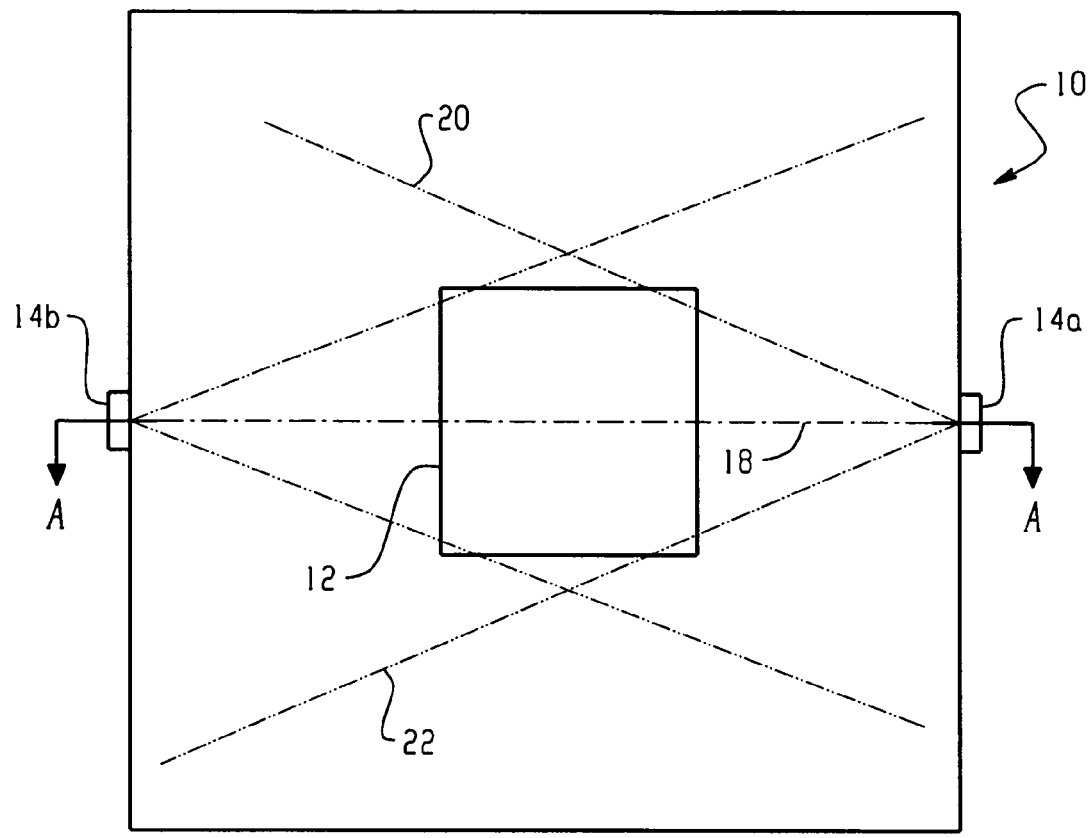
FIG. 1 is an illustration of a window in a viewing system suitable for embodying the principles of the present invention.
Figure 2:
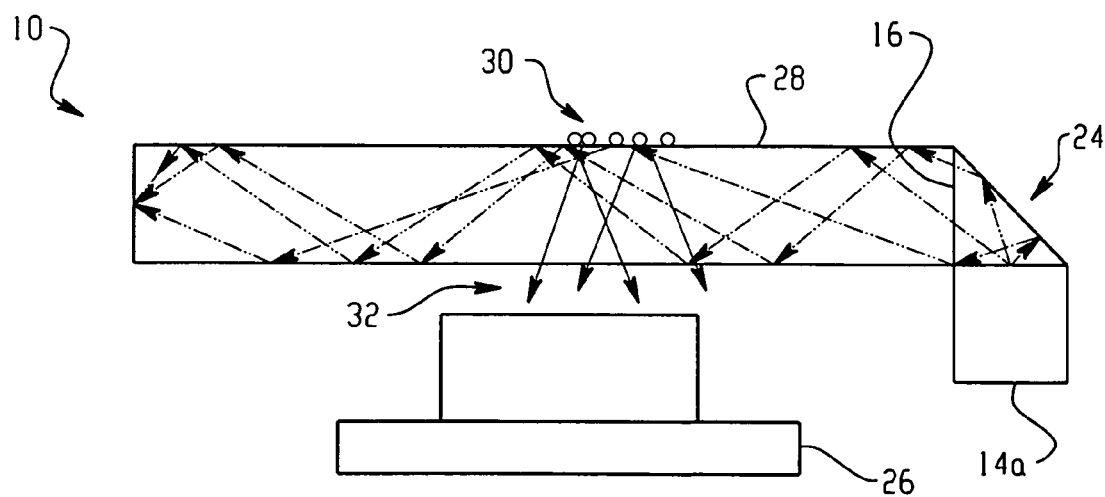
FIG. 2 is a cross-sectional view of the window including an embodiment of an aspect of the present invention.
Figure 3:
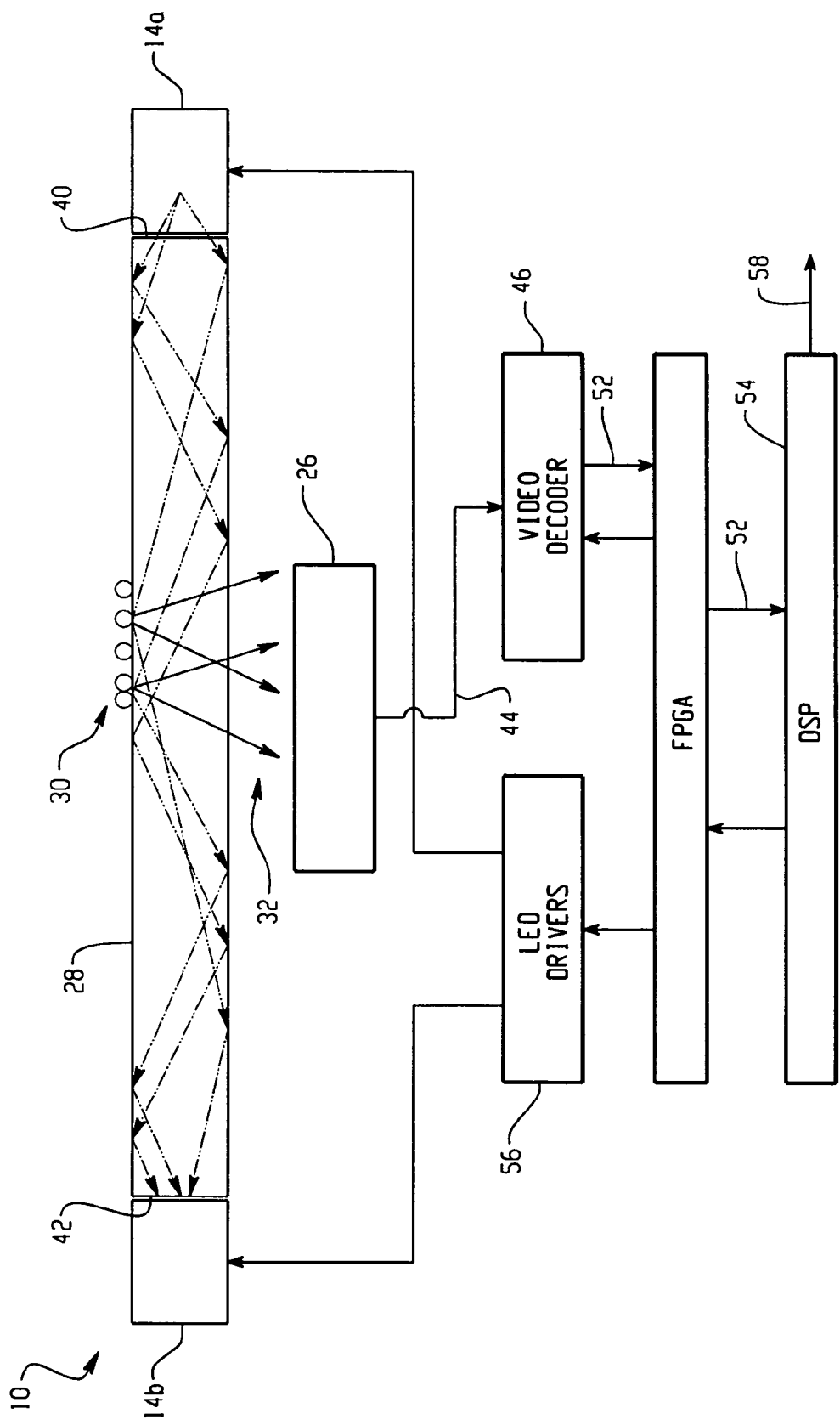
FIG. 3 is a cross-sectional view of the window including an embodiment of another aspect of the present invention.

The present invention utilizes light to detect contaminants in a viewing area of a window of a viewing system. Various embodiments of the invention are shown in FIGS. 1, 2 and 3. Referring to FIG. 1, a window 10 which may be made of glass, for example, is disposed in front of a camera which views a scene through a viewing area 12 thereof. The window 10 is provided to protect the camera and other components of the viewing system from the environment of the scene being viewed. FIG. 2 is a cross-sectional view of one embodiment of the present invention. Referring to the cross-sectional view of FIG. 2 which is along the cut A—A of FIG. 1, a light source 14a which may be a light emitting diode (LED) or laser chip, for example, is disposed to inject light into an edge side 16 of the window 10, preferably along an axis 18 (see FIG. 1) which bisects the viewing area 12. The window edge 16 may be polished to improve the coupling efficiency of the light from source 14a into the window 10.

The light source 14a may be directly coupled or reflected into the window 10. In the embodiment of FIG. 2, light is reflected from the source 14a into the window 10 by a mirrored prism 24 to minimize the size requirements of the overall sensing apparatus. The mirrored prism 24 and light source 14a may be mounted together and to window 14 by refractive index matching epoxy, for example. A light detector 26, which may be an area imager like a charge coupled detector (CCD) or a photoelectric array detector, for example, is positioned behind the viewing area 12 of the window 10 to capture and measure the intensity of light impinging thereon. In the present embodiment, the light detector comprises a CCD with a 500×800 array of detecting elements or pixels. The wavelength of the light source 14a is chosen to be optimized to the CCD detector. In this embodiment, the light source generates a light beam at a wavelength of 880 nanometers with a bandwidth on the order of 50 nanometers.

The beam of light from source 14a will be injected into the window from side 16 and pass along the axis 18 (see FIG. 1). In the present embodiment, as the light beam moves away from side 16, the beam width will spread at approximately ±40° to the axis 18 as shown by the light rays 20 and 22 in FIG. 1 and cover most of the viewing area 12. As light passes through the window 10, some of the light will be reflected back into the window and travel through the window 10 as shown by the arrowed lines in FIG. 2. Other injected light passes through the window surface 28. As the passed light strikes particulates 30 in the viewing area 12 of the surface 28, the light is scattered and reflected. Some of the light from the particulates 30 is reflected back through the window 10 as shown by the arrowed lines 32 and captured by the CCD 26 which generates a data stream of electrical signals representative of the captured light intensity of the pixels of the CCD array. The pixel data stream of the CCD 26 may be further processed by components of the viewing system to detect the particulates 30 on the surface 28 of the window 10 as will be described in greater detail herein below in connection with the embodiment of FIG. 3.

In another embodiment, multiple light sources 14 may be utilized to improve light signal strength or intensity captured by the CCD 26 and/or to provide for redundancy. In the exemplary embodiment of FIG. 3 which shows a cross-sectional view of window 10 along the cut A—A of FIG. 1, two LED light sources 14a and 14b are disposed at opposite side edges of the window 10 to inject light directly into the window 10 along the axis 18 (see FIG. 1). The side edges 40 and 42 which couple light from the LED sources 14a and 14b, respectively, into the window 10 are each polished to improve light coupling efficiency. Light injected into window 10 from the source 14b will spread through window 10 to cover the viewing area 12 (see FIG. 1) in the same manner as has been described for light source 14a in the embodiment of FIG. 2.

In the embodiment of FIG. 3, the apparatus for detecting contaminants on the surface 28 of the window 10 utilizes existing components of a viewing system which may be infrared video or the like. For this embodiment, the CCD 26 is utilized both as the detector of contaminants and as the camera of the viewing system. The data stream of pixel signals generated by the CCD 26 is conducted over signal line 44 to a video decoder 46 wherein the pixel signals are digitized and formatted into an image frame of rows and columns. The video decoder 46 may be of the type manufactured by Analog Devices, under the model no. ADV7179, for example. A Field Programmable Gate Array (FPGA) 48, which may be of the type manufactured by Xilinx, under the model no. XC2S200E, for example, is programmed with the logic circuitry to perform the timing and control of the viewing system in cooperation with the processing of a digital signal processor (DSP) 54. For example, the FPGA 48 may control the video decoder 46 to output the frame formatted digitized pixel data serially over signal line 52 to the DSP 54 for further processing. The DSP 54 may be of the type manufactured by Texas Instruments, under the model no. TMS320C6414, for example. Also, the FPGA 48 may control LED driver circuits 56 to cause light to be injected into the window 10 in a timely manner.

In an exemplary operation, the DSP 54 via the FPGA 48 may direct the collection of one or more frames of pixel data from the CCD 26 without injecting light into the window. The DSP 54 will process the collected pixel data to establish reference data for any background or stray light in the viewing scene of the CCD 26. Then, the DSP 54 via FPGA 48 may direct the LED driver circuits to cause light to be injected into the window 10 through one or both of the polished side edges 40 and 42. During the time of light injection, the DSP 54 via the FPGA 48 may direct the collection of one or more frames of pixel data from the CCD 26 to establish uncompensated measurement data which will include the light 32 reflected from the particulates 30 and the background and stray light of the viewing scene. The DSP 54 may thereafter subtract the collected reference light intensity data from the uncompensated measurement data on a pixel by pixel basis to establish a measurement of contamination of the viewing area 12 compensated for background and stray light in the viewing scene. The compensated contaminated measurement data may be used to estimate the number of pixels having intensity values that could possibly be affected by the contaminants on the viewing area of the window and thus, distort the images acquired by the viewing or imaging system.

Figure 4:
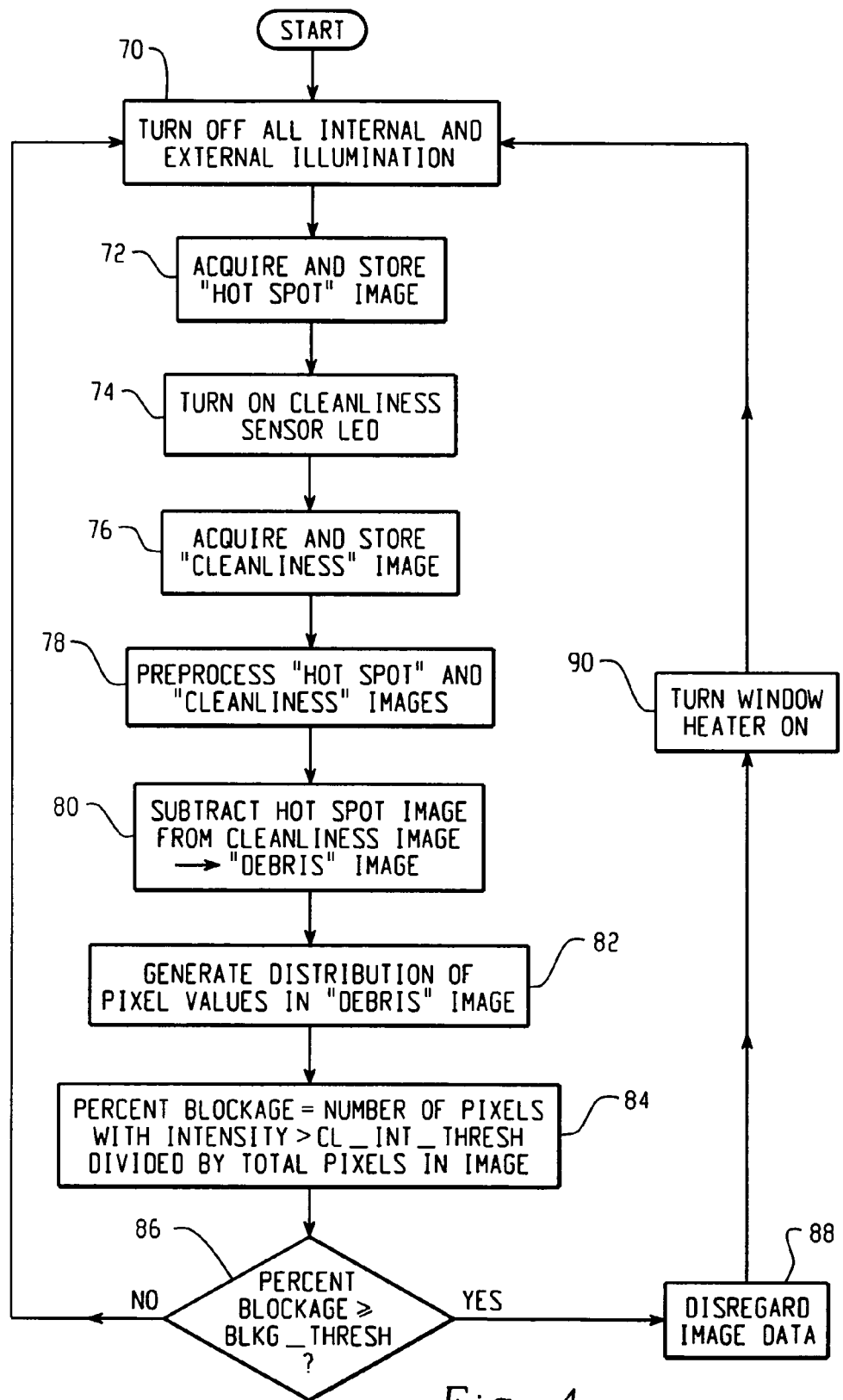
FIG. 4 is a flow chart of an exemplary algorithm suitable for embodying yet another aspect of the present invention.

The aforementioned operation may be embodied in an algorithm for execution by the DSP 54. A flowchart of an exemplary algorithm for this purpose is shown in FIG. 4. In the exemplary embodiment, the algorithm utilizes two distinct images acquired by the CCD 26 or other image acquisition device. The first image is intended to capture light sources, to which the camera or image acquisition device (i.e. CCD, etc.) is sensitive, that are in the camera or imager's view, and that are not under the control of the viewing system to which the camera or imager belongs. For example, an illuminated lightbulb in the camera or imager's view might appear in this image. To achieve this effect, in block 70 of the flowchart, all internal and external illumination under the system's control are turned "off". Under these conditions, the first image is captured from the CCD 26 via the video decoder 46 and stored in a memory of the DSP 54 in block 72. The first image will be referred to herein after as the 'hot spot image' because an external light source not under control of the system, like a fluorescent light, for example, will show up in a clump of high intensity, contiguous pixels as a bright spot in the image.

Thereafter, in block 74, under these conditions, the sensor's light source(s) is(are) turned "on" and, in block 76, the second image utilized by this algorithm is captured in the same manner as the first image and also stored in a memory of the DSP 54. The second image, which is referred to herein as the 'cleanliness image', is intended to contain the same light sources as the hot spot image, but also contain light reflected into the imaging device by contamination or debris on the viewing area of the window. It is preferred that the cleanliness image be captured a very short amount of time (for example, 33 ms) after the hot spot image is captured. This will minimize the effects of a moving or variable hot spot on this algorithm, i.e. keep the bright spot in the same clump of pixels in both images.

In order to reduce the effects of normal CCD noise on the algorithm, both the hot spot image and the cleanliness image may be preprocessed in some manner in block 78. One possible method of preprocessing the images would be to apply an averaging filter to each image. This smoothes out some of the noise inherent to CCD's or other image acquisition device. Other methods of preprocessing may also be done in addition to or in place of averaging filters. If the viewing system does not suffer from noticeable noise in the acquired images, preprocessing may not be necessary.

Since light from the window light source(s) is reflected back to the CCD imager by contaminants or debris on the window, a measure of how much debris is present will depend on the number of pixels that are bright in the cleanliness image. However, if an exterior illumination source is present, the light seen by the imager as a result of it may be confused for light reflected off of debris. To reduce the likelihood of this happening, in block 80, the (possibly preprocessed) hot spot image is subtracted from the (possibly preprocessed) cleanliness image to produce a resulting image which will be referred to as the 'debris image' which may also be stored in a memory of the DSP 54. The remaining pixels with high intensity in the debris image should all be caused by light reflecting off actual contaminants or debris on the window.

Figure 5:
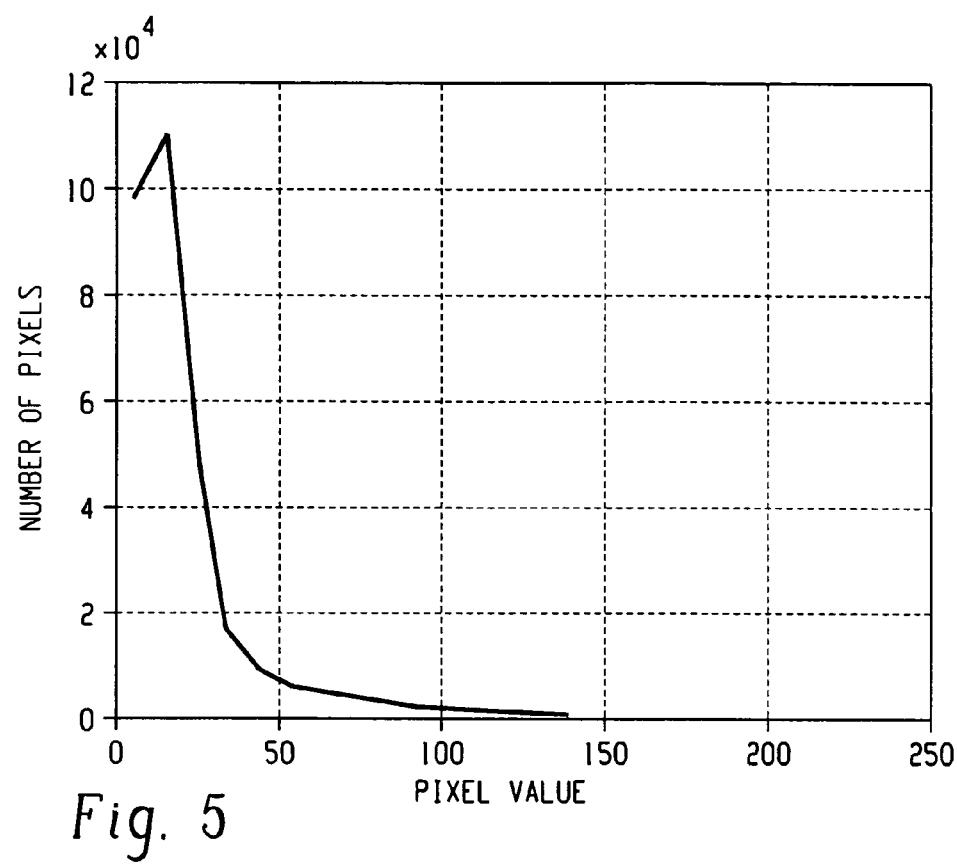
FIG. 5 is a graph exemplifying a first distribution of pixel values suitable for use in the example algorithm of FIG. 4.
Figure 6:
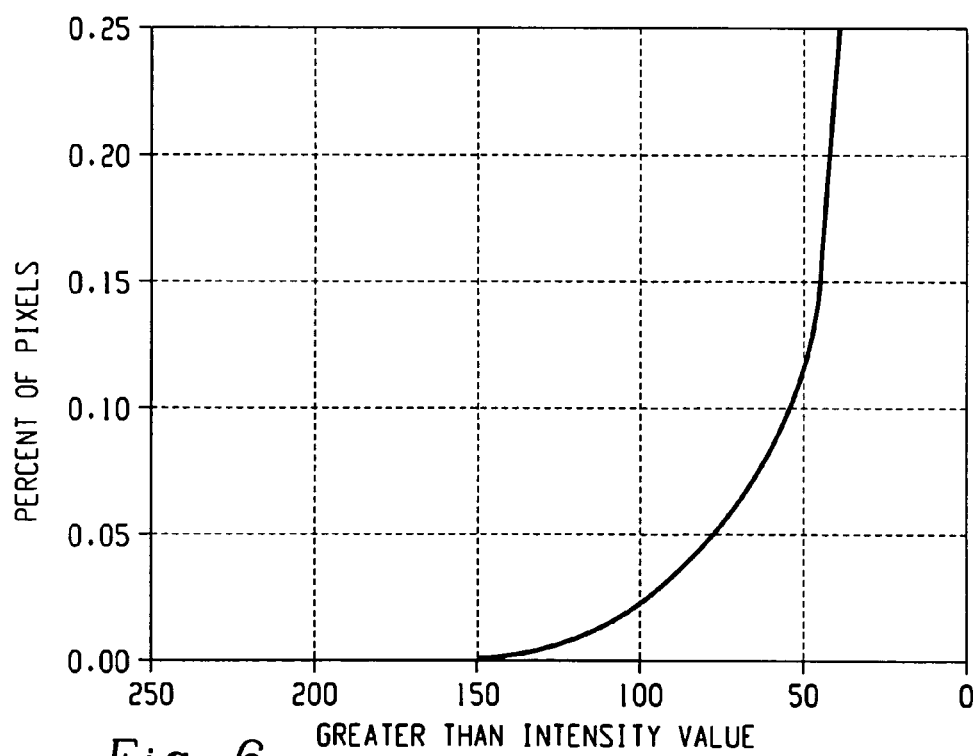
FIG. 6 is a graph exemplifying a second distribution of pixel values suitable for use in the example algorithm of FIG. 4.

In the next block 82, the debris image is used by the DSP 54 to generate a distribution of pixel values resulting from debris on the viewing area of the window. This distribution may be a standard histogram, relating the number of pixels with a given intensity value present in the debris image. FIG. 5 shows an exemplary histogram of a contaminated image. From this histogram, the DSP 54 may generate in block 84 a second distribution (see FIG. 6 for an example) that shows how many pixels are present in the debris image with pixel values greater than or equal to a given or threshold intensity value (cl_int_thresh). The user of the system may select a 'pixel intensity threshold', above which a pixel (window section) is considered 'contaminated', and below which a pixel (window section) is considered 'clean'. (This intensity threshold is preferably selected experimentally by placing debris on the window and comparing the intensity of the resulting compensated image pixels with the amount by which the debris blocks external light from reaching the pixels.)

With this second distribution, it is determined how many pixels in the compensated image have intensities greater than or equal to this threshold, and thus how many pixels are 'contaminated'. In the present embodiment, the count (#) of how many pixels in the compensated image have intensities greater than or equal to the intensity threshold is converted to a % blockage in block 84 by dividing this count by the total number of pixels in the image. If the % blockage of a debris image is equal to or exceeds a user-defined maximum blockage threshold (blkg_thresh) as determined by decisional block 86, then the contamination sensor alerts the system to take appropriate action such as disregarding the current image data in block 88 and/or activating a heater or window cleaner in block 90, for example. Execution always continues, so as to always measure cleanliness. Only other image processing is affected if the window is dirty.

In addition to the approach described above, other useful information, such as the mean, standard deviation, etc. of the pixel intensity values in the compensated image could be generated, supplied to the user, or used in a different method of determining contaminants on the window which could obscure the acquired image.

While the present invention has been described herein above in connection with one or more embodiments, it is understood that such description is provided merely by way of example. Accordingly, the above described embodiments should not be considered to limit the invention in any way. Rather, the present invention should be construed in breadth and broad scope in accordance with the recitation of the claims appended hereto.

What is claimed is:

1. Method of detecting contaminants on a window surface of a viewing system, said method comprising the steps of: injecting light edgewise into the window to cause said light to pass internally through the window from one window edge side to another window edge side along an axis which intersects a viewing area of the window, some of said injected light being passed through the window surface and reflected from contaminants in said viewing area of said surface;

capturing said reflected light in an image;
converting said image into image data;
detecting said contaminants on said window surface from said image data; the limitation generating a signal indicative of the contaminants on said window surface.

2. The method of claim 1 wherein the step of injecting includes reflecting light off of contaminants on an outside surface of the window back through the window and inside surface thereof.

3. The method of claim 1 wherein the step of capturing includes capturing the reflected light in an area image comprising a plurality of pixels; and wherein the step of converting includes converting said pixels of the image into electrical data representative of the image.

4. The method of claim 1 including the step of compensating said image data for background light in a scene of the viewing system.

5. The method of claim 1 including the steps of: capturing a first image of a scene of the viewing system excluding the reflected light; converting said first image into first image data; capturing a second image of said scene including the reflected light; converting said second image into second image data; and compensating said second image data with said first image data.

6. The method of claim 5 wherein the step of compensating includes subtracting the first image data from the second image data to produce compensated image data.

7. The method of claim 5 wherein the compensated image data comprises a multiplicity of pixel light intensity values; and including the steps of: determining a number of pixel light intensity values in the compensated image data that are greater than a predetermined value; and determining if the contaminants on the window surface will affect a scene image of the viewing system based on said number of pixel light intensity values.

8. The method of claim 5 including the step of capturing the first and second images within a short time interval of each other.

9. The method of claim 1 including determining if the detected contaminants on the window surface will affect a scene image of the viewing system.

10. Apparatus for detecting contaminants on an external surface of a window of a viewing system, said apparatus comprising:

at least one light source disposed to inject light edgewise into the window to cause said light to pass internally through the window from one window edge side to another window edge side along an axis which intersects a viewing area of the window, some of said injected light being passed through the external window surface and reflected from contaminants in said viewing area of said surface back through the window and internal surface thereof;
an imager for capturing an image of said reflected light and converting said image into image data; and
a processor for processing said image data to detect said contaminants on said external surface.

11. The apparatus of claim 10 wherein the processor is operative to determine if the detected contaminants will affect a scene image of the viewing system.

12. The apparatus of claim 10 wherein the at least one source is controllable off and on; wherein the imager is operative to capture a first image of a scene of the viewing system when the at least one light source is controlled off and to capture a second image of said scene when the at least one light source is controlled on; and wherein the processor is further operative to receive first image data and second image data from the imager and to compensate said second image data with said first image data to produce compensated image data.

13. The apparatus of claim 12 wherein the compensated image data comprises a multiplicity of pixel light intensity values; and wherein the processor is operative to detect contaminants on the window surface based on pixel light intensity values exceeding a predetermined value.

14. The apparatus of claim 13 wherein the processor is operative to determine a number of pixel light intensity values in the compensated image data that exceed the predetermined value and to determine if the contaminants on the window surface will affect a scene image of the viewing system based on said number.

15. The apparatus of claim 14 wherein the processor is operative to generate a signal indicative of a condition in which contaminants on the window surface will affect a scene image of the viewing system.

16. The apparatus of claim 10 wherein the at least one light source comprises a light emitting diode.

17. The apparatus of claim 10 wherein the imager comprises a charge coupled device.

18. A viewing system comprising:
a window for protecting the viewing system from an environment of a scene viewable by the system;
an imager disposed behind said window for capturing images of said scene through a viewing area of said window and for converting said captured images into electrical image data;
at least one light source disposed to inject light edgewise into said window to cause reflections of the injected light off of contaminants on said window surface, said imager also for capturing images of said scene including said light reflected from said contaminants; and
a processor for processing both of said electrical image data of said scene excluding reflected light from said contaminants, and electrical image data of said scene including reflected light from said contaminants to detect said contaminants on said external surface and to determine if the detected contaminants will affect the electrical image data of said scene.

19. The viewing system of claim 18 wherein the processor is operative to control an on and off operation of said at least one light source.

20. The viewing system of claim 18 wherein the processor is operative to compensate the image data of the scene including the reflected light with image data of the scene excluding the reflected light to produce compensated image data, and to detect contaminants on the window surface based on the compensated image data.

21. The viewing system of claim 20 wherein the compensated image data comprises a multiplicity of pixel intensity values; and wherein the processor is operative to detect contaminants on the window surface by comparing the pixel intensity values of the compensated image data with a predetermined value.

22. The viewing system of claim 21 wherein the processor is operative to determine a number of pixel intensity values of the compensated image data that are greater than the predetermined value, and to determine whether or not to disregard a scene image based on said number.

23. The viewing system of claim 21 wherein the processor is operative to determine a number of pixel intensity values of the compensated image data that are greater than the predetermined value, and to determine whether or not to effect a cleansing of said window based on said number.

24. The viewing system of claim 18 wherein the at least one light source and imager are controlled to effect capture of the image of the scene excluding reflected light from the contaminants, and the image of the scene including reflected light from the contaminants within a short time interval of each other.

25. The viewing system of claim 18 including a digitizer for converting image data from the imager into digital image data; and wherein the processor comprises a digital signal processor for processing the digital image data in accordance with a programmed algorithm.

* * * * *